(12) United States Patent
Sakuma et al.

(10) Patent No.: US 11,172,837 B2
(45) Date of Patent: Nov. 16, 2021

(54) FORMING WEARABLE STACKED STRAIN GAUGE SENSOR FOR MONITORING

(71) Applicant: International Business Machines Corporation, Armonk, NY (US)

(72) Inventors: Katsuyuki Sakuma, Fishkill, NY (US); Jeffrey D. Gelorme, Burlington, CT (US); Marlon Agno, Scarsdale, NY (US)

(73) Assignee: International Business Machines Corporation, Armonk, NY (US)

( * ) Notice: Subject to any disclaimer, the term of this patent is extended or adjusted under 35 U.S.C. 154(b) by 309 days.

(21) Appl. No.: 16/164,264

(22) Filed: Oct. 18, 2018

(65) Prior Publication Data

US 2020/0121204 A1 Apr. 23, 2020

(51) Int. Cl.
*A61B 5/024* (2006.01)
*A61B 5/022* (2006.01)
*G01L 1/22* (2006.01)
*A61B 5/00* (2006.01)

(52) U.S. Cl.
CPC ...... *A61B 5/02444* (2013.01); *A61B 5/02241* (2013.01); *A61B 5/6826* (2013.01); *G01L 1/2287* (2013.01); *A61B 5/4082* (2013.01); *A61B 2562/0247* (2013.01)

(58) Field of Classification Search
CPC .......................... A61B 5/02444; A61B 5/02241
See application file for complete search history.

(56) References Cited

U.S. PATENT DOCUMENTS

| 6,236,037 B1 | 5/2001 | Asada et al. |
| 6,236,572 B1 * | 5/2001 | Teshome ............... H05K 1/0219 174/261 |
| 7,094,061 B1 * | 8/2006 | Kieffer ................. G01L 5/0047 439/65 |
| 7,096,748 B2 * | 8/2006 | Kutlu .................... G01L 5/0047 73/862.474 |
| 8,574,510 B2 | 11/2013 | Gofman et al. |
| 9,301,712 B2 | 4/2016 | McNames et al. |

(Continued)

FOREIGN PATENT DOCUMENTS

EP 0535508 A1 4/1993

OTHER PUBLICATIONS

Kim et al., "Miniaturized Battery-Free Wireless Systems for Wearable Pulse Oximetry," Advanced Functional Materials, vol. 27, No. 1 (Nov. 2016) (14 pages).

(Continued)

*Primary Examiner* — Minh N Trinh
(74) *Attorney, Agent, or Firm* — Daniel Morris; Michael J. Chang, LLC

(57) ABSTRACT

In one aspect, forming a stacked strain gauge sensor with increased electrical resistance includes: forming multiple sensor layers, wherein the sensor layers include strain gauge sensor wires on substrates; forming holes in the substrates; stacking the sensor layers, one on top of another, to form a stack with the holes aligned in one or more locations forming through holes in the stack; and forming interconnects in the holes in one or more other locations interconnecting the strain gauges sensor wires between adjacent sensor layers to form a stacked strain gauge sensor. A stacked strain gauge sensor and method of use thereof are also provided.

13 Claims, 10 Drawing Sheets

(56) References Cited

U.S. PATENT DOCUMENTS

| | | | |
|---|---|---|---|
| 9,302,046 | B1 | 4/2016 | Giuffrida et al. |
| 2006/0282021 | A1 | 12/2006 | DeVaul et al. |
| 2007/0294890 | A1* | 12/2007 | Gisin ............ H01L 23/49827 333/33 |
| 2010/0241015 | A1 | 9/2010 | Petrasek et al. |
| 2018/0085061 | A1 | 3/2018 | Heisig et al. |
| 2020/0121204 | A1* | 4/2020 | Sakuma ............ A61B 5/1072 |

OTHER PUBLICATIONS

Vega, "Monitoring Parkinson's Disease Progression Using Behavioral Inferences, Mobile Devices and Web Technologies", Conference: 25th International Conference Companion on World Wide Web, at Montreal, Canada, Apr. 2016, pp. 323-327.

Mascaro et al., "Photoplethysmograph Fingernail Sensors for Measuring Finger Forces Without Haptic Obstruction," IEEE Transactions on Robotics and Automation, vol. 17, No. 5, pp. 698-708 (Oct. 2001).

Mascaro et al., "Understanding of Fingernail-Bone Interaction and Fingertip Hemodynamics for Fingernail Sensor Design," Proceedings 10th Symposium on Haptic Interfaces for Virtual Environment and Teleoperator Systems. HAPTICS 2002, (Feb. 2002) (9 pages).

Kao et al., "NailO: Fingernails as an Input Surface," Proceedings of the 33rd Annual ACM Conference on Human Factors in Computing Systems, Apr. 2015 (5 pages).

Dierk et al., "AlterNail: Ambient, Batteryless, Stateful, Dynamic Displays at your Fingertips," CHI 2017, pp. 6754-6759 (May 2017).

Zeiser et al., "Capacitive strain gauges on flexible Polymer substrates for wireless, intelligent systems," J. Sens. Sens. Syst., 3, pp. 77-86 (Apr. 2014).

Houghton et al., "Stretchable Capacitive Strain Sensors Based on a Novel Polymer Composite Blend," 2017 IEEE 67th Electronic Components and Technology Conference, pp. 2263-2268 (May/Jun. 2017).

* cited by examiner

FORMING WEARABLE STACKED STRAIN
GAUGE SENSOR FOR MONITORING

FIELD OF THE INVENTION

The present invention relates to flexible and wearable sensors, and more particularly, to easily-detachable, stacked strain gauge sensors with increased electrical resistance.

BACKGROUND OF THE INVENTION

Wearable devices such as those mounted on surfaces such as the fingernails allow for the collection and analysis of quantitative, clinically relevant information on physiological status. See Kim et al., "Miniaturized Battery-Free Wireless Systems for Wearable Pulse Oximetry," Advanced Functional Materials, vol. 27, no. 1 (November 2016). These devices have the potential to establish chronic interfaces (i.e., months) on hard surfaces such as the fingernails. A biocompatible adhesive bonds the device to the body. The adhesive ensures strong adhesion to the fingernail.

However, when it comes time to take the devices off, the removal process is tedious and time consuming. A solvent is applied to device to release the adhesive. Removal can however take up to 30 minutes or even more before the adhesive fully releases from the nail. Oftentimes, repeat soakings in the solvent are needed. This removal process is impractically long.

Further, a surface such as the fingernail provides a limited surface area. Thus, the device is constrained to a limited overall footprint. Working within these dimensional constraints can be challenging.

SUMMARY OF THE INVENTION

The present invention provides flexible and wearable yet easily-detachable, stacked strain gauge sensors with increased electrical resistance. In one aspect of the invention, a method of forming a stacked strain gauge sensor is provided. The method includes: forming multiple sensor layers, wherein the sensor layers include strain gauge sensor wires on substrates; forming holes in the substrates; stacking the sensor layers, one on top of another, to form a stack with the holes aligned in one or more locations forming through holes in the stack; and forming interconnects in the holes in one or more other locations interconnecting the strain gauges sensor wires between adjacent sensor layers to form a stacked strain gauge sensor. The stacked strain gauge sensor can have a footprint with dimensions of less than or equal to 15 mm×15 mm, enabling the stacked strain gauge sensor to be attached to a body surface such as fingernail using an adhesive.

In another aspect of the invention, a stacked strain gauge sensor is provided. The stacked strain gauge sensor includes: multiple sensor layers stacked, one on top of another, wherein the sensor layers include strain gauge sensor wires on substrates; holes in the substrates, wherein the holes are aligned in one or more locations forming through holes in the stack; and interconnects in the holes in one or more other locations interconnecting the strain gauges sensor wires between adjacent sensor layers. Each of the substrates can include: a film (e.g., a polyurethane film, a polyester film and/or a polyimide film) and an adhesive layer (e.g., an acrylate and/or acrylic adhesive).

In another aspect of the invention, a method of using stacked strain gauge sensors is provided. The method includes: attaching one or more stacked strain gauge sensors to at least one body surface using an adhesive, wherein each of the one or more stacked strain gauge sensors has i) multiple sensor layers stacked, one on top of another, wherein the sensor layers include strain gauge sensor wires on substrates, ii) holes in the substrates, wherein the holes are aligned in one or more locations forming through holes in the stack, and iii) interconnects in the holes in one or more other locations interconnecting the strain gauges sensor wires between adjacent sensor layers; collecting data from the one or more stacked strain gauge sensors; and applying an adhesive remover via the through holes to release the one or more stacked strain gauge sensors from the at least one body surface.

A more complete understanding of the present invention, as well as further features and advantages of the present invention, will be obtained by reference to the following detailed description and drawings.

DETAILED DESCRIPTION OF PREFERRED EMBODIMENTS

Figure 1:
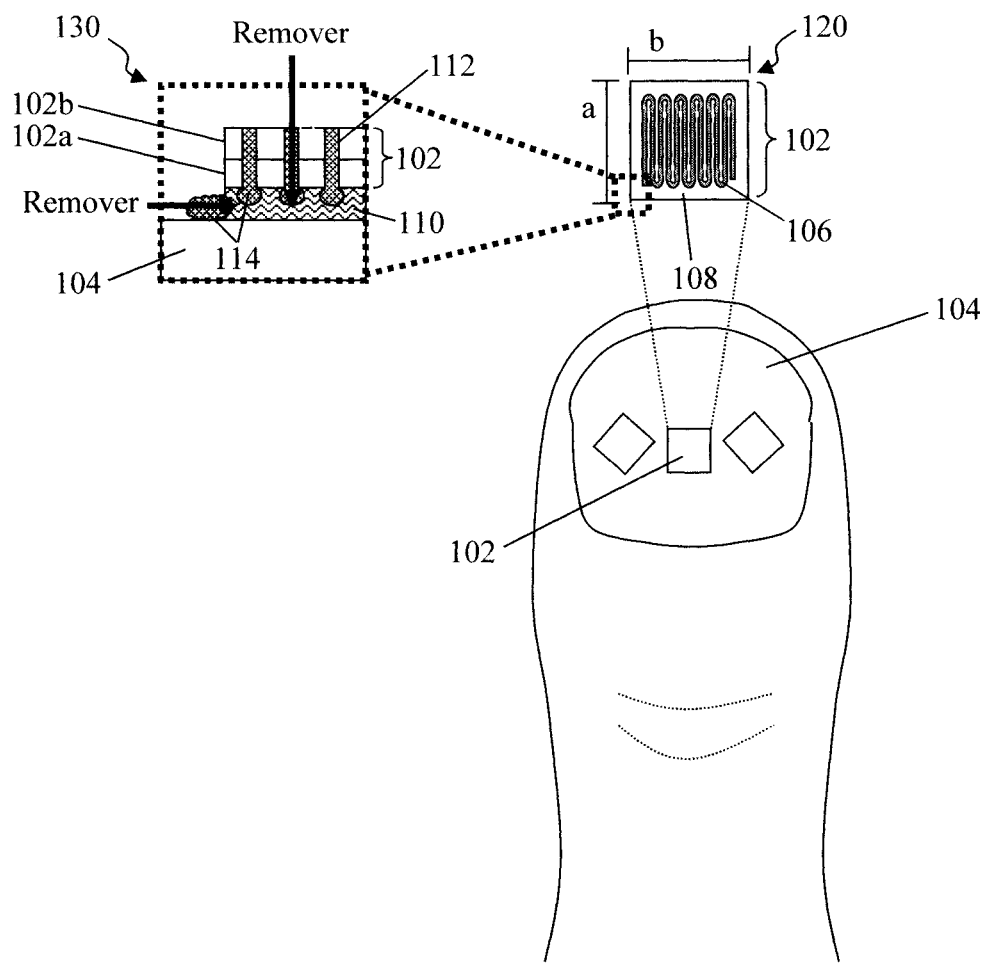
FIG. 1 is a diagram illustrating at least one of the present strain gauge sensors attached to a body surface (e.g., a fingernail) according to an embodiment of the present invention.

Provided herein are wearable yet easily-detachable, stacked strain gauge sensors with increased electrical resistance. By "wearable," it is meant that the present strain gauge sensors can be attached to a body surface such as to fingernails or other parts of the body using an adhesive. For instance, by way of example only, the present stacked strain gauge sensors can be attached to nails (e.g., fingernails, toenails, animal claws, etc.), teeth, bones, hands, foreheads, arms, legs, chest, head, on human beings and/or animal subjects.

When attached to a body surface(s), the present strain gauge sensors can be employed to measure changes in the contour of the body surface to which the strain gauge sensors are attached based on a measurement of the piezo-resistive effect generated by the strain gauge sensors. See, for example, U.S. Patent Application Publication Number 2018/0085061 by Heisig et al., entitled "Characterizing Primate Nail Deformation" (hereinafter "U.S. Patent Application Publication Number 2018/0085061"), the contents of which are incorporated by reference as if fully set forth herein. For instance, when attached to the fingernails, the present stacked strain gauge sensors can measure: direct force such as when the finger is pressed directly downward against an object making the finger nail less convex, left and right shear (transverse) forces such as when the finger is pressed against an object and moved left or right making the nail deformation more pronounced on one side, positive and negative longitudinal forces such as when the finger is pressed against an object and positively or negatively in the longitudinal direction causing the nail to arch or bow. See, for example, U.S. Patent Application Publication Number 2018/0085061.

The ability to measure these contour changes via the present stacked strain gauge sensors has a variety of important clinical applications. For instance, patients with degenerative neurological conditions such as Parkinson's disease experience motor symptoms such as tremors and rigidity. When evaluating patients with such neurological conditions it is important to have an efficient and effective way to evaluate their treatment effectiveness and the progression of their symptoms. The present stacked strain gauge sensors, can, for example, be employed as a Unified Parkinson's Disease Rating Scale (UPDRS) for daily neurological examinations such as based on finger-tapping test. See, for example, U.S. Patent Application Publication Number 2018/0085061.

As provided above, body surfaces such as the fingernail provides a limited surface area for the sensors. For instance, a human fingernail has a surface area of approximately 15 millimeter (mm)×15 mm. Thus, the sensor footprint is constrained to this area and must be designed accordingly.

One notable design constraint is sensor resistance. Increasing the electrical resistance advantageously decreases the total current and power consumption of the sensor. However, to increase the resistance, the size of the sensor needs to be increased (i.e., a longer wire equates with a higher resistance). For wearable sensors, the size of the device is limited by the footprint dimensions (e.g., 15 mm×15 mm). Advantageously, unique sensor designs are provided herein where higher electrical resistance is achieved by stacking several strain gauge layers. For instance, if the resistance is 100 ohms (Ω) per layer, then stacking three layers increases the overall resistance in the strain gauge sensor to 300Ω. As will be described in detail below, electrodes in each of the stacked layers are connected using vertical interconnections. The number of stacked layer can be varied to tune resistance without any increase in the footprint of the strain gauge sensor, e.g., beyond 15 mm×15 mm.

As also provided above, the implementation of a wearable sensor device requires that the device adhere robustly to the body surface. For instance, a biocompatible adhesive can be used to attach the sensor to the body surface, such as to the fingernail. The adhesive-backed sensor must remain securely attached for the duration of the data collection process which can span minutes to days or even months, depending on the particular application.

However, once it comes time for removal, it is desirable to be able to reverse the bonding effects of the adhesive as quickly as possible. That way the device is more user-friendly and easier to implement, for example, in clinical settings where a doctor, nurse or other clinician would benefit from easier application and instant removal of the device from a patient (e.g., where removal takes from 30 seconds to 3 minutes and ranges therebetween, for example from 30 seconds to 1 minute and ranges therebetween). A liquid adhesive remover such as a solvent like acetone and/or gamma-butyrolactone (GBL) can be applied to release the bond of the adhesive. However, with limited access to bonding surfaces beneath the sensor, the adhesive remover takes a significant amount of time to work, sometimes from 5 minutes to 30 minutes or even more, and may require multiple applications (i.e., multiple soakings in the adhesive remover). Namely, the adhesive remover typically only has access to the outer edges of the bonding interface and must then permeate along this interface, working from the outside in, to release the bond.

Advantageously, unique sensor designs are provided herein where the strain gauge contains through holes that enable the liquid adhesive remover to pass at multiple points through the body of the sensor and down to the bonding interface, thus providing multiple pathways for the adhesive remover to release the bond. As such, removal of the present strain gauge from the body surface(s) is quick and easy.

For instance, according to an exemplary embodiment, an acrylate and/or acrylic adhesives such as cyanoacrylate (CA) glue cyanoacrylate (CA) glue is used to adhere the present strain gauge sensors to the body surfaces such as the fingernails. The area of the glue mount is important for removal time of the glue. A pathway for the adhesive remover (such as a solvent like acetone and/or GBL) into the glue matrix must be provided for rapid removal. This pathway into the glue matrix is provided via the through holes.

See, for example, FIG. 1. As shown in FIG. 1, at least one of the present strain gauge sensors 102 is attached to a body surface (in this case a fingernail 104). In the present example, multiple strain gauge sensors 102 are attached to the same body surface (e.g., to the same fingernail) optionally at different orientations/locations. However, embodiments are contemplated herein where a single strain gauge sensor is employed.

Further, FIG. 1 illustrates how the footprint of the present strain gauge sensor can be configured to fit on the respective body surface (e.g., 15 mm×15 mm or less for a human fingernail 104). For instance, in the present example, each strain gauge sensor 102 is smaller than the respective fingernail 104 to which it is attached, thereby enabling multiple strain gauge sensors 102 to be attached to the same fingernail 104. Namely, according to an exemplary embodiment, the footprint of the present strain gauge sensor a×b (see FIG. 1) is less than or equal to 15 mm×15 mm. However, that configuration is merely an example, and the size of the present strain gauge sensors can be scaled up or down depending on the particular application.

A magnified view 120 of one of the strain gauge sensors 102 is provided. In general, each strain gauge sensor includes multiple (stacked) layers, each layer having a metal sensor wire 106 on a flexible substrate 108. As will be described in detail below, embodiments are contemplated herein where the flexible substrate includes multiple layers, such as a backing film bonded to a cover film by an adhesive. As shown in FIG. 1, the sensor wire 106 is configured to have a serpentine layout which increases the length of the sensor wire 106, and hence the resistance. However, with the constraints on the overall footprint of the strain gauge sensor (see above), the length of the sensor wire 106 can only be made so long. To increase the overall resistance, and thereby decrease the total current and power consumption of the sensor, multiple sensor layers 102a, 102b, etc. are stacked. See cross-sectional sideview 130 provided in FIG. 1. As will be described in detail below, interconnects are used between the layers to connect the sensor wires 106 from each of the layers together. As highlighted above, the depiction of a sensor stack having two layers is merely an example, and embodiments are contemplated herein having a sensor stack with more than two interconnected layers.

As also shown in cross-sectional sideview 130, an adhesive 110 (e.g., cyanoacrylate glue) is used to attach the stacked strain gauge sensor 102 to the body surface (i.e., fingernail 104). The adhesive 110 is present between the bottom-most layer (i.e., layer 102a in the present example) and the fingernail 104 surface. In order to facilitate removal of the stacked strain gauge sensor 102, through holes 112 are present that pass through each of the layers (102a, 102b, etc.) of the stacked strain gauge sensor 102 at multiple locations throughout the body of the sensor stack, thus providing multiple pathways for an adhesive remover 114 (e.g., acetone and/or GBL) to permeate the matrix of the adhesive 110 and release the bond. Action of the adhesive remover 114 will also be along the lateral sides of the adhesive 110, thus release of the adhesive 110 occurs on multiple fronts making removal of the present strain gauge from the body surface(s) quick and easy.

Figure 2:
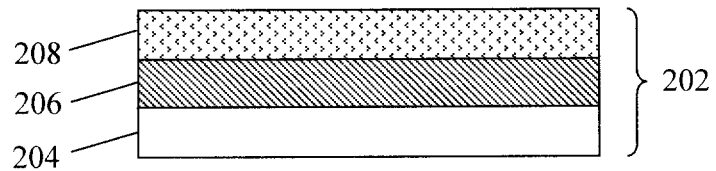
FIG. 2 is a cross-sectional diagram illustrating a flexible substrate having a cover film and a backing film attached to the cover film by an adhesive layer according to an embodiment of the present invention.

An exemplary methodology for forming the present stacked strain gauge sensors is now described by way of reference to FIGS. 2-12. As highlighted above, the present strain gauge sensor stack is built on a flexible substrate. This flexible substrate can include multiple layers. For instance, as shown in FIG. 2, a flexible substrate 102 is provided including a cover film 204 (acting as a cover film over the fingernail or other body surface to which the stacked strain gauge sensor is attached) and a backing film 208 attached to the cover film 204 by an adhesive layer 206.

Suitable materials for the cover film 204 include, but are not limited to, polyethylene terephthalate (PET), poly-coated (e.g., polyethylene-coated) and/or silicone-coated, bleached, Kraft paper. For instance, in one embodiment, the cover film 204 is a release film such as a Kraft paper film coated with a silicone release agent. The release film is oriented with the silicone release agent proximal to the adhesive layer 206. When stacking the sensor layers (see below), the cover film 204 can simply be removed from the top sensor layer (via the releasing agent), exposing the adhesive layer 206. The exposed adhesive layer 206 enables bonding of the top sensor layer to a bottom sensor layer(s) forming the stacked strain gauge sensor design. According to an exemplary embodiment, the cover film 204 has a thickness of from 20 micrometers (μm) to 100 μm and ranges therebetween.

Suitable backing film 208 materials include, but are not limited to, polyurethane films, polyester films, and/or polyimide films such as Kapton® available from DuPont, Wilmington, Del. According to an exemplary embodiment, the backing film 208 has a thickness of from 10 μm to 100 μm and ranges therebetween.

Suitable adhesives for layer 206 include, but are not limited to, acrylate and/or acrylic adhesives such as cyanoacrylate (CA) glue. According to an exemplary embodiment, the adhesive layer 206 has a thickness of from 10 μm to 100 μm and ranges therebetween.

Figure 3:
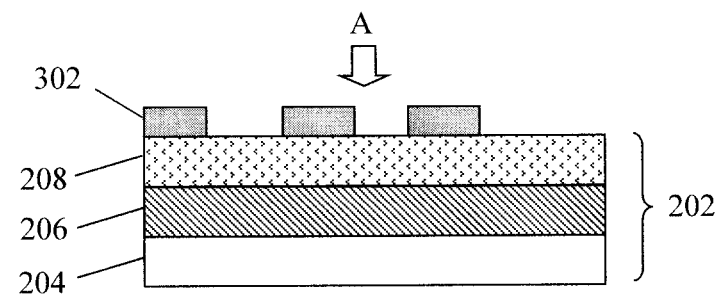
FIG. 3 is a cross-sectional diagram illustrating a sensor wire having been deposited onto the substrate forming a first/top sensor layer according to an embodiment of the present invention.

As shown in FIG. 3, a sensor wire 302 is deposited on the substrate 202. Suitable materials for the sensor wire 302 include, but are not limited to, electrically conductive paste materials such as silver (Ag)-containing pastes, copper (Cu)-containing pastes, carbon-containing pastes, metals such as silver (Ag), copper (Cu) and/or aluminum (Al), metal alloys such as copper-nickel alloys, e.g., constantans ($Cu_{60}Ni_{40}$), nickel-chromium alloys, e.g., chromel ($Ni_{65}Fe_{25}Cr_{10}$), copper-manganese-nickel alloys, e.g., Manganine® ($Cu_{84}Mn_{12}Ni_4$), and/or doped semiconductor materials such as n-type or p-type doped silicon (Si). Suitable n-type dopants include, but are not limited to, phosphorous (P) and/or arsenic (As), and suitable p-type dopants include, but are not limited to, boron (B). According to an exemplary embodiment, the sensor wire 302 has a thickness of from 1 μm to 20 μm and ranges therebetween.

A variety of different techniques are contemplated herein for depositing the sensor wire 302 on the substrate 202. For instance, according to one embodiment, the sensor wire 302 is printed onto the substrate 202 using an automated dispensing tool such as a 3-axis automated fluid dispensing robot available from Nordson EFD, Westlake, Ohio. The tool is employed to dispense/print an (electrically) conductive ink onto the substrate 202 forming the sensor wire 302. By way of example only, suitable conductive inks include, but are not limited to, DuPont 5025 silver conductor for flexible substrates, available from DuPont, Wilmington, Del., which has a sheet resistivity of from 12 milliohms per square (mΩ/sq) to 15 mΩ/sq and a viscosity of from 20 Pascal-second (Pa·S) to 30 Pa·S. This process can be used to print the sensor wire 302 having any desired shape, including the serpentine configuration described above.

According to another exemplary embodiment, metals or metal alloys such as Ag, Cu, Al, copper-nickel alloys, nickel-chromium alloys, copper-manganese-nickel alloys, etc. (see above) can be deposited onto the substrate 202 by a process such as evaporation or sputtering using a metal mask to form the sensor wire 302. By this process, the sensor wire 302 can be formed having any desired shape, including the serpentine configuration described above. Alternatively, according to yet another exemplary embodiment, a preformed metal/metal alloy or doped semiconductor sensor wire 302 can be attached to the substrate 202 using a biocompatible adhesive. Suitable biocompatible medical adhesives are commercially available, for example, from Henkel, Dusseldorf, Germany.

Figure 4:
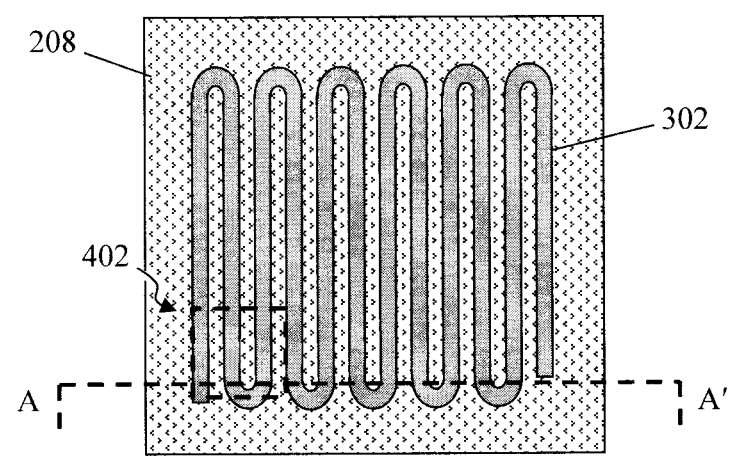
FIG. 4 is a top-down diagram illustrating an exemplary serpentine configuration of the sensor wire of FIG. 3 according to an embodiment of the present invention.

FIG. 4 provides a top-down view (e.g., from viewpoint A—see FIG. 3) of an exemplary configuration of the sensor wire 302. In this particular example, the sensor wire 302 has a serpentine configuration. It is noted that FIG. 3 provides a cross-sectional view (along A-A') of a section 402 of the sensor layer.

Figure 5:
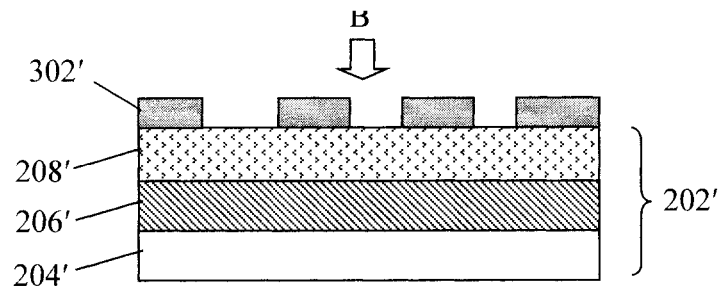
FIG. 5 is a cross-sectional diagram illustrating an additional, second/bottom sensor layer having been formed according to an embodiment of the present invention.

The sensor wire 302 on substrate 202 forms one layer of the present stacked strain gauge sensor design. The process is iterated to fabricate at least one more sensor layer in the same manner as described above. Namely, as shown in FIG. 5, an additional sensor layer has been formed (as described above) including a sensor wire 302' on a substrate 202'. As above, the substrate includes a cover film 204' and a backing film 208' attached to the cover film 204' by an adhesive layer 206'. Suitable materials, dimensions, etc. for the sensor wire and these substrate layers were provided above. For ease and clarity of description, the sensor wire 302 on substrate 202 will also be referred to herein as a "top sensor layer" and sensor wire 302' on a substrate 202' will also be referred to herein as a "bottom sensor layer" since the former will be stacked on the latter (see below). It is also to be understood that one or more additional sensory layers may be included in between the top sensor layer and the bottom sensor layer.

Figure 6:
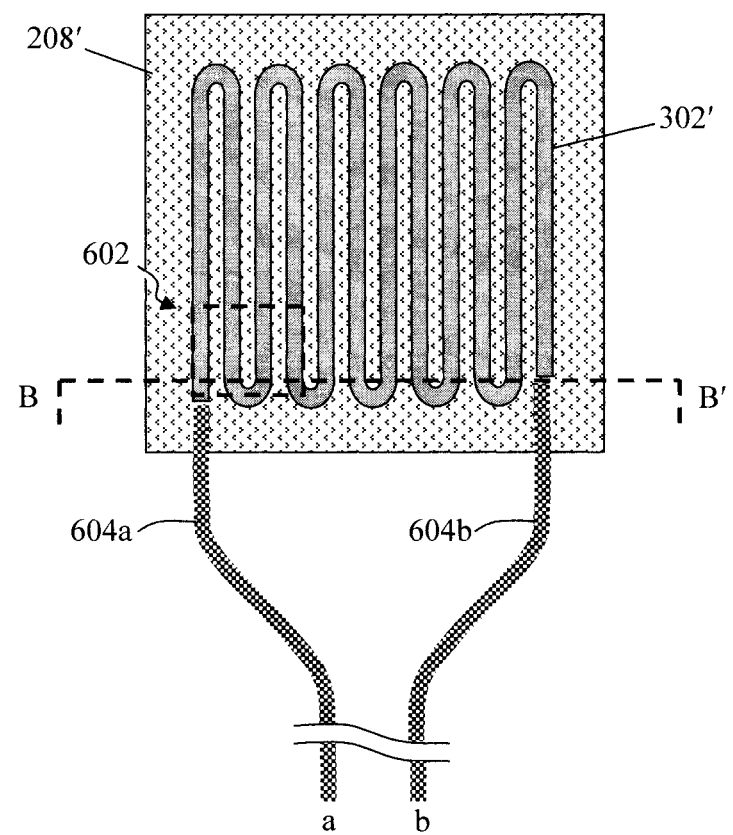
FIG. 6 is a top-down diagram illustrating an exemplary serpentine configuration of the sensor wire of FIG. 5 according to an embodiment of the present invention.

FIG. 6 provides a top-down view (e.g., from viewpoint B—see FIG. 5) of an exemplary configuration of the sensor wire 302'. In this particular example, the sensor wire 302' has a serpentine configuration. It is noted that FIG. 5 provides a cross-sectional view (along B-B') of a section 602 of the sensor layer. As shown in FIG. 6, wires 604a,b are attached to opposite ends of the sensor wire 302'. Wires 604a,b serve to connect the stacked strain gauge sensor (e.g., at points a and b) to a Wheatstone bridge circuit (see for example FIG. 13—described below). Since the sensor wires 302, 302' of the stacked sensor layers will be interconnected (see below), wires 604a,b are needed for connection to only one of the sensor layers, i.e., the bottom sensor layer in this example. In that case, the top sensor layer (see FIG. 4) does not have these wires. The wires 604a,b can be formed from any suitable electrical conductor such as a metal(s), e.g., Ag, Cu, Al, etc. which can be different from the material used for the sensor wire.

Holes 702/802 are then created in the substrates 202/202'. See FIG. 7 and FIG. 8, respectively. According to an exemplary embodiment, holes 702/802 are formed in the substrates 202/202' using a laser. For instance, in one non-limiting example the following laser parameters were employed: fluence: $1.154 \times 10^9$ millijoules per centimeter squared ($mJ/cm^2$) with 15% attenuation (power: 2.4 watts (W) and laser diameter: 15 µm), number of pulses: 2, frequency: 41 megahertz (MHz), and recipe: 150 cycles.

Figure 7:
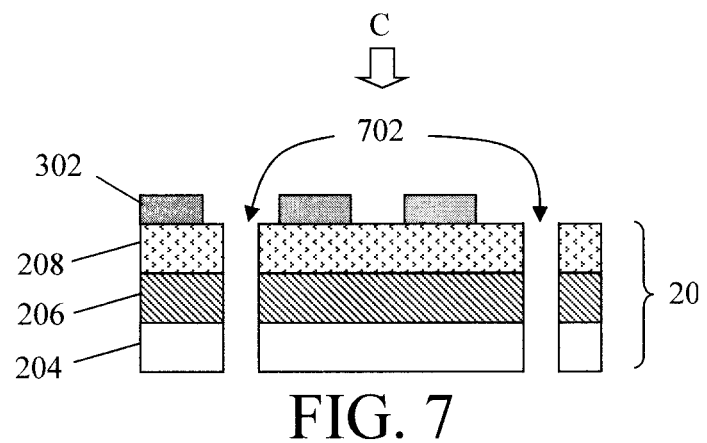
FIG. 7 is a cross-sectional diagram illustrating holes having been created in the substrate of the first/top sensor layer according to an embodiment of the present invention.
Figure 8:
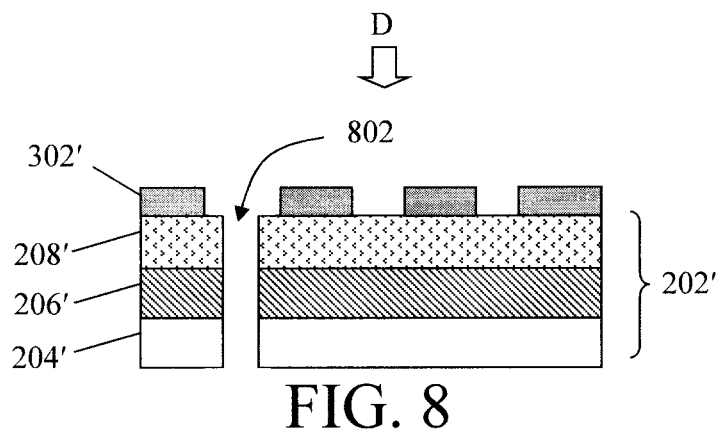
FIG. 8 is a cross-sectional diagram illustrating holes having been created in the substrate of the second/bottom sensor layer according to an embodiment of the present invention.

As shown in FIG. 7 and FIG. 8, the holes 702/802 extend completely through the respective substrates 202/202'. As will become apparent from the description that follows, the holes 702 and 802 in one or more locations will align to form through holes for access by the adhesive remover, whereas the holes 702 in one or more other locations extend only through the top sensor layer and provide access for interconnect formation between the sensor layers.

Figure 9:
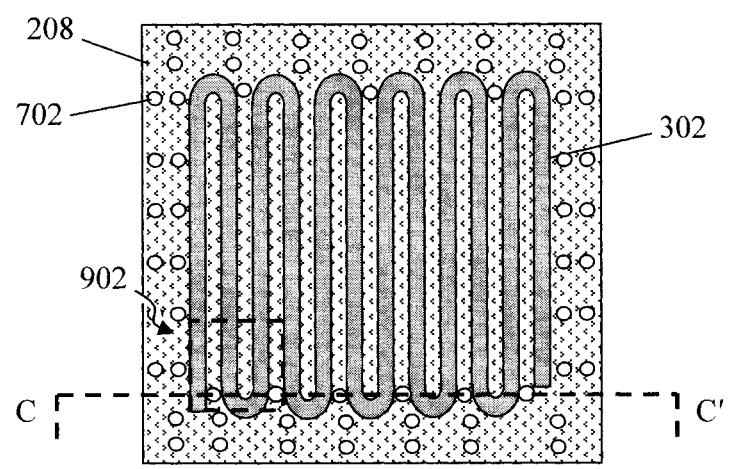
FIG. 9 is a top-down diagram illustrating the holes created in the substrate of the first/top sensor layer according to an embodiment of the present invention.
Figure 10:
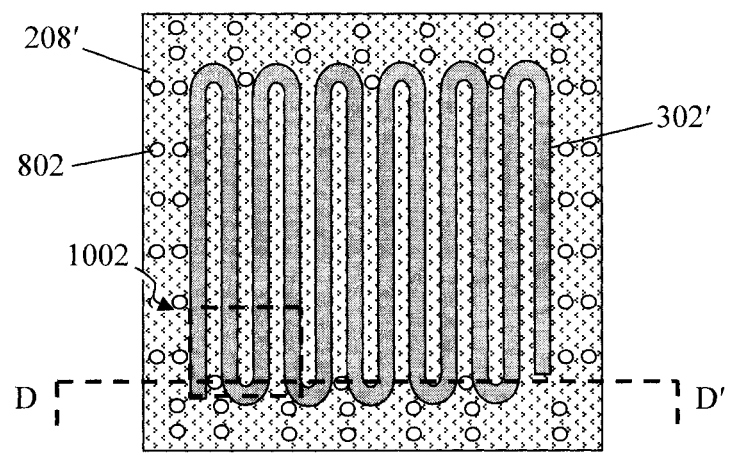
FIG. 10 is a top-down diagram illustrating the holes created in the substrate of the second/bottom sensor layer according to an embodiment of the present invention.

FIG. 9 and FIG. 10 provide top-down views (e.g., from viewpoints C and D—see FIG. 7 and FIG. 8, respectively) of the top sensor layer having holes 702 and the bottom sensor layer having holes 802, respectively. It is noted that FIG. 7 and FIG. 8 provide cross-sectional views (along C-C') of a section 902 and (along D-D') of a section 1002 of the top/bottom sensor layers, respectively.

Figure 11:
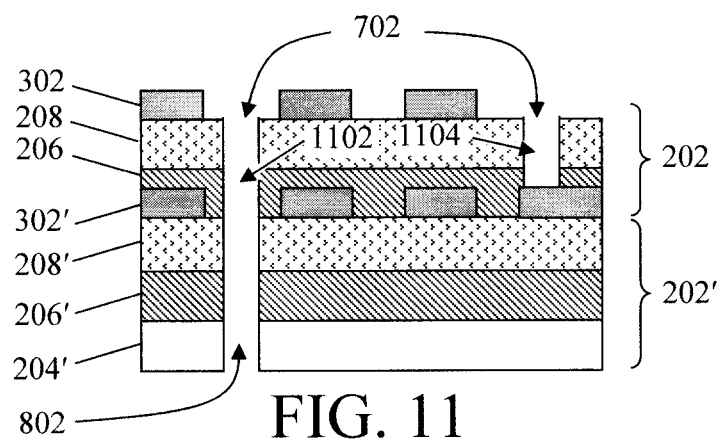
FIG. 11 is a cross-sectional diagram illustrating the top/bottom sensor layers having been stacked, one on top of the other, with the holes in the top sensor layer being aligned with one or more of the holes in the bottom sensor layer in one or more locations forming through holes in the stack according to an embodiment of the present invention.

The sensor layers are then stacked, one on top of the other. See FIG. 11. As shown in FIG. 11, the top sensor layer (i.e., sensor wire 302 on substrate 202) is bonded to the bottom sensor layer (i.e., sensor wire 302' on substrate 202') via the adhesive layer 206. As provided above, the cover film 204 can be configured as a release film coated with a release agent. In that case, when stacking the sensor layers, the cover film 204 can simply be removed from the top sensor layer (via the release agent), exposing the adhesive layer 206. The exposed adhesive layer 206 is then used to bond the top sensor layer to the bottom sensor layer forming the stacked strain gauge sensor.

As also shown in FIG. 11, the top sensor layer (i.e., sensor wire 302 on substrate 202) is positioned on the bottom sensor layer (i.e., sensor wire 302' on substrate 202') with the holes 702 in the top sensor layer being aligned with one or more of the holes 802 in the bottom sensor layer in one or more locations. These aligned holes 702/802 form through holes 1102 extending through the sensor stack. As provided above, these through holes 1102 provide access for an adhesive remover (e.g., acetone and/or GBL) when it comes time to detach the sensor from the body surface. The action of an adhesive remover via these through holes was depicted in FIG. 1, described above.

As further shown in FIG. 11, the holes 702 in the top sensor layer do not align with one of the holes 802 in the bottom sensor layer in one or more other locations. These holes 702 will provide conduits 1104 for interconnects between the layers. As will be described in detail below, the interconnects will interconnect the sensor wires 302/302' in adjacent layers of the stack. Thus, according to an exemplary embodiment, the conduits 1104 for the interconnects are present over the sensor wire of the underlying layer. See FIG. 11.

Figure 12:
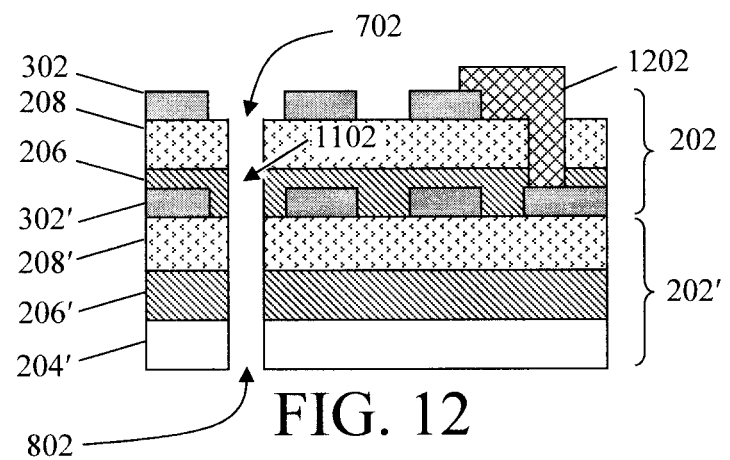
FIG. 12 is a cross-sectional diagram illustrating interconnects having been formed in the holes in one or more other locations that interconnect the sensor wires in adjacent layers of the stack according to an embodiment of the present invention.

Next, an interconnect(s) 1202 is formed in the conduits 1104. See FIG. 12. As shown in FIG. 12, the interconnect(s) 1202 are in contact with both the sensor wire 302 of the top sensor layer and the sensor wire 302' of the bottom sensor layer. Suitable materials for the interconnect(s) 1202 include, but are not limited to, metals and/or metal alloys such as copper (Cu), platinum (Pt), nickel (Ni), tin (Sn), lead (Pb), indium (In), tin-silver (SnAg), tin-silver-copper (SnAgCu), tin-bismuth (TiBi), gold-tin (AuSn), zinc-tin (Zn—Sn), and/or lead-tin (PbSn). For instance, according to an exemplary embodiment, the interconnect(s) 1202 are formed using a eutectic solder alloy such as a PbSn alloy.

Optionally, a protective layer can be applied to the top of the sensor stack to prevent mechanical and chemical damage caused by exposure to the elements such as water, humidity, etc. According to an exemplary embodiment, formation of this protective layer begins with a cover film 1304/adhesive layer 1306/backing film 1308 like the cover film 204, 204'/adhesive layer 206, 206'/backing film 208, 208' configurations described above. See FIG. 13.

As above, suitable materials for the cover film 1304 include, but are not limited to, PET, poly-coated (e.g., polyethylene-coated) and/or silicone-coated, bleached, Kraft paper. For instance, the cover film 1304 can be a release film such as a Kraft paper film coated with a silicone release agent proximal to the adhesive layer 1306. According to an exemplary embodiment, the cover film 1304 has a thickness of from 20 µm to 100 µm and ranges therebetween. Suitable materials for the adhesive layer 1306 include, but are not limited to, acrylate and/or acrylic adhesives such as cyanoacrylate (CA) glue. According to an exemplary embodiment, adhesive layer 1306 has a thickness of from 10 µm to 100 µm and ranges therebetween. Suitable materials for the backing film 1308 include, but are not limited to, polyurethane films, polyester films, and/or polyimide films such as Kapton® available from DuPont, Wilmington, Del. According to an exemplary embodiment, the backing film 1308 has a thickness of from 10 µm to 100 µm and ranges therebetween.

Figure 13:
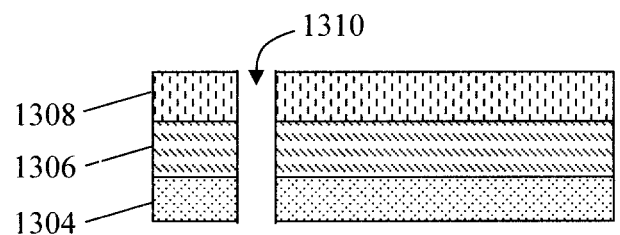
FIG. 13 is a cross-sectional diagram illustrating a hole(s) having been formed in a protective layer according to an embodiment of the present invention.

In order provide access for the adhesive remover, the through holes 1102 need to extend through the sensor stack (including the protective layer in this example). Thus, as shown in FIG. 13, at least one hole 1310 is formed in the cover film 1304/adhesive layer 1306/backing film 1308. Like holes 702/802, hole(s) 1310 can be created in these layers using a laser. Exemplary laser parameters were provided above.

Figure 14:
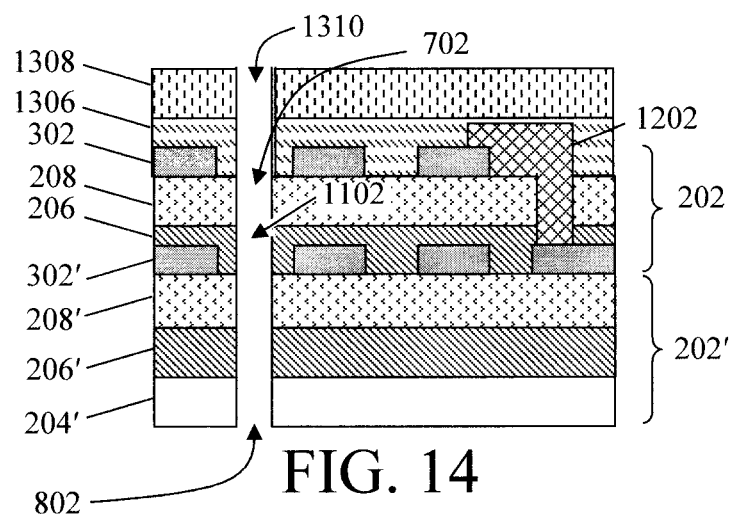
FIG. 14 is a cross-sectional diagram illustrating the protective layer having been bonded to the top of the stack according to an embodiment of the present invention.

As provided above, the cover film 1304 can be a release film. In that case, the cover film 1304 is removed (via the releasing agent) to expose the adhesive layer 1306 and, as shown in FIG. 14, the backing film 1308 is bonded via the exposed adhesive layer 1306 to the top sensor layer over the sensor wire 302 and interconnect(s) 1202. The backing film 1308 serves as the protective layer over the underlying sensor layers. Care is taken to align the hole(s) 1310 with one or more of the holes 702/802 in the top/bottom sensor layers forming the through holes 1102 that extend completely through the sensor stack and protective layer.

Figure 15:
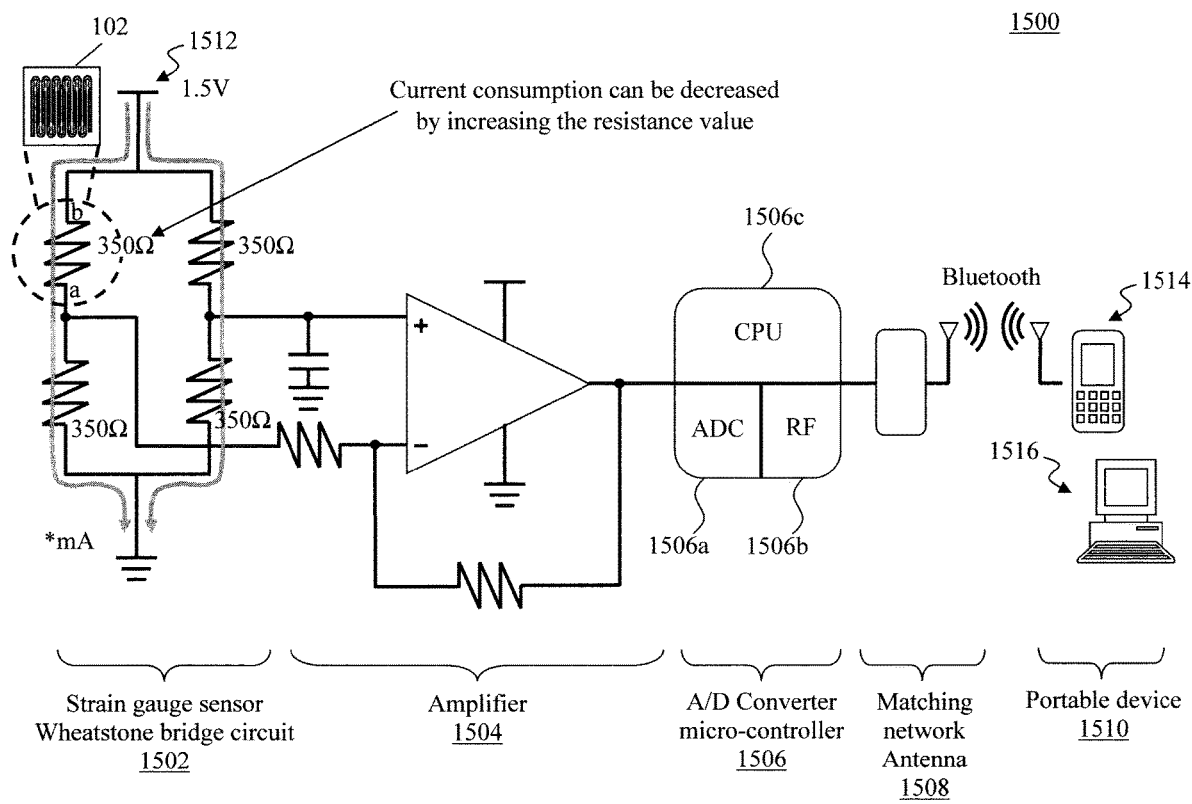
FIG. 15 is a diagram illustrating an exemplary system employing the present stacked strain gauge sensors according to an embodiment of the present invention.

An exemplary system 1500 employing the present stacked strain gauge sensors is depicted schematically in FIG. 15. System 1500 includes a strain gauge sensor and Wheatstone bridge circuit 1502, an amplifier 1504, an analog to digital converter, a module 1506 that includes an analog to digital converter 1506a (i.e., ADC), a radio frequency (RF) controller 1506b and a micro-controller 1506c, a network antenna 1508, and a portable device 1510. As shown in FIG. 15, at least one of the present stacked strain gauge sensors 102 serves as a resistor in Wheatstone bridge circuit 1502. As provided above, by stacking the sensor layers, an increase in sensor resistance can be achieved without increasing the overall sensor footprint. Advantageously, increasing the resistance decreases the overall power consumption. As shown in FIG. 15, Wheatstone bridge circuit 1502 receives power from power supply 1512. It is notable that the values (i.e., power supply, resistance, etc.) shown in FIG. 15 are merely given as examples and not intended to in any way limit the embodiments to these particular values.

Amplifier 1504 serves to amplify the (voltage) signal output from the Wheatstone bridge circuit 1502. Analog to digital converter 1506a (i.e., ADC) in module 1506 converts that amplified signal into a digital signal. Module 1506 can also include a micro-controller 1506c (e.g., a processor—CPU) that prepares (e.g., conditions, buffers, etc.) the signal for the radio frequency (RF) controller 1506b that then transfers the digitized signals to a receiver.

Network antenna 1508 transmits the digital signals from analog to digital converter 1506. These digital signals are transmitted, for example, via near-field communication (NFC), WiFi, Bluetooth® technology, etc. to one or more user devices, such as a smartphone 1514 (or other smart devices such as a smartwatch, smart glasses, etc.) and/or computer 1516.

Figure 16:
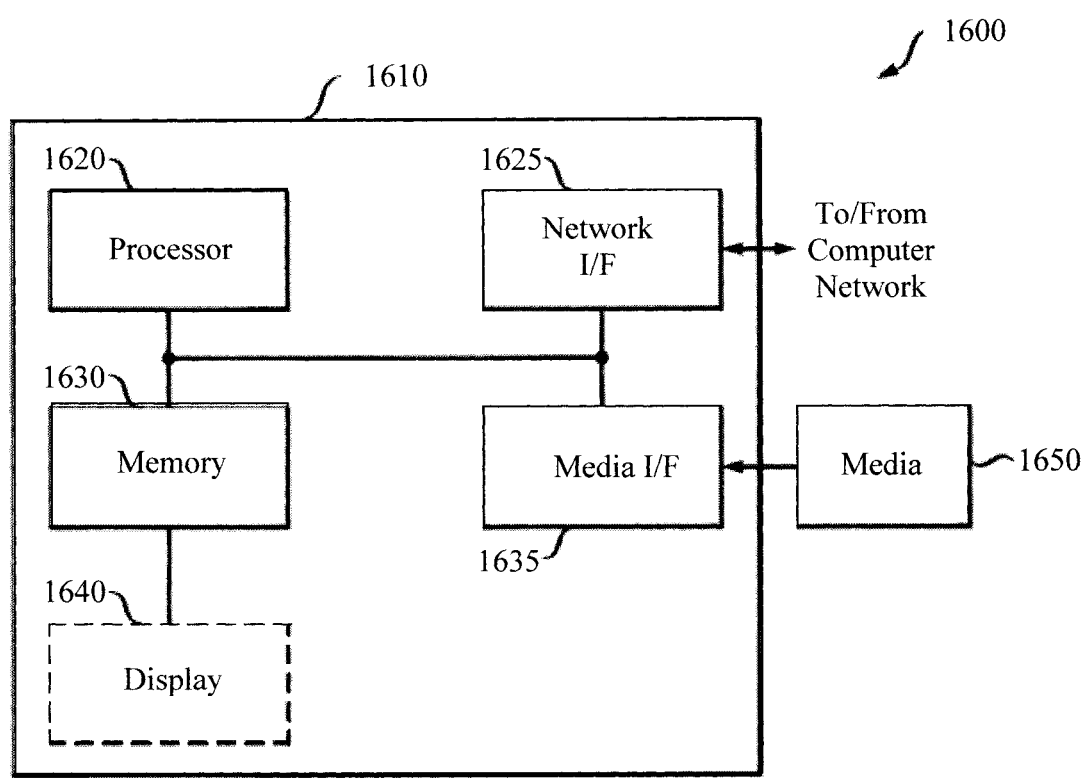
FIG. 16 is a diagram illustrating an exemplary apparatus for performing one or more of the methodologies presented herein according to an embodiment of the present invention.

Turning now to FIG. 16, a block diagram is shown of an apparatus 1600 for implementing one or more of the techniques presented herein. By way of example only, apparatus 1600 can be configured to serve as the micro-controller 1606c and/or as one or more of the user devices (e.g., smartphone 1614, computer 1616, etc.) of system 1600 (FIG. 16).

Apparatus 1600 includes a computer system 1610 and removable media 1650. Computer system 1610 includes a processor device 1620, a network interface 1625, a memory 1630, a media interface 1635 and an optional display 1640. Network interface 1625 allows computer system 1610 to connect to a network, while media interface 1635 allows computer system 1610 to interact with media, such as a hard drive or removable media 1650.

Processor device 1620 can be configured to implement the methods, steps, and functions disclosed herein. The memory 1630 could be distributed or local and the processor device 1620 could be distributed or singular. The memory 1630 could be implemented as an electrical, magnetic or optical memory, or any combination of these or other types of storage devices. Moreover, the term "memory" should be construed broadly enough to encompass any information able to be read from, or written to, an address in the addressable space accessed by processor device 1620. With this definition, information on a network, accessible through network interface 1625, is still within memory 1630 because the processor device 1620 can retrieve the information from the network. It should be noted that each distributed processor that makes up processor device 1620 generally contains its own addressable memory space. It should also be noted that some or all of computer system 1610 can be incorporated into an application-specific or general-use integrated circuit.

Optional display 1640 is any type of display suitable for interacting with a human user of apparatus 1600. Generally, display 1640 is a computer monitor or other similar display.

Figure 17:
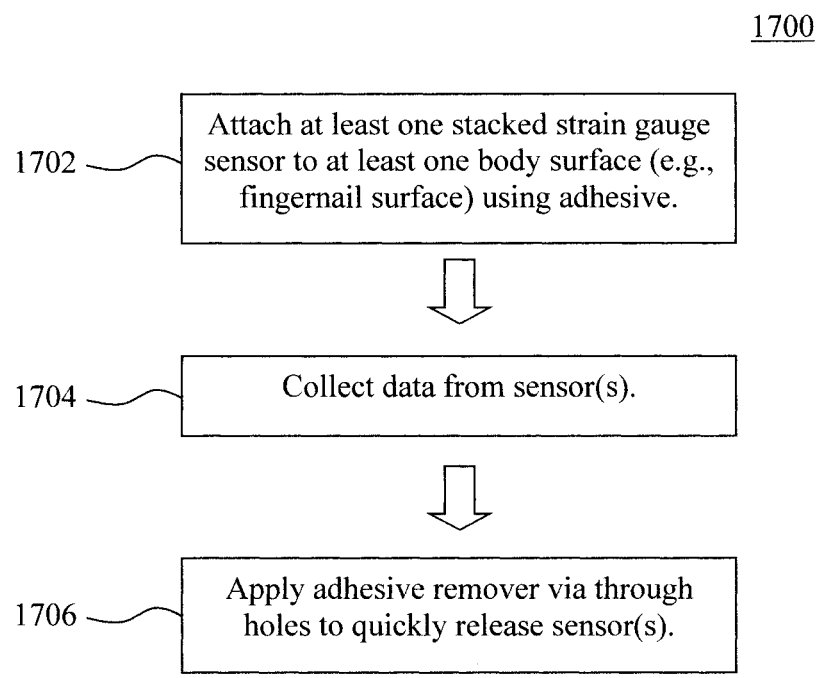
FIG. 17 is a diagram illustrating an exemplary methodology for using the present stacked strain gauge sensors according to an embodiment of the present invention.

FIG. 17 is a diagram illustrating an exemplary methodology 1700 for using the present stacked strain gauge sensors. In step 1702, at least one of the stacked strain gauge sensors is attached to at least one body surface using a suitable bio-compatible adhesive. As provided above, suitable adhesives include, but are not limited to, acrylate and/or acrylic adhesives such as cyanoacrylate glue. The stacked strain gauge sensors employed in this embodiment are fabricated using the above-described techniques, and thus include a stack of sensor layers (each having a strain gauge sensor wire on a substrate), through holes in the stack in one or more locations (for permeation of the adhesive remover), and interconnects in one or more other locations of the stack that interconnect the strain gauges sensor wires between adjacent sensor layers.

In step 1704, data is collected from the sensor(s). By way of example only, the stacked strain gauge sensors can be part of a system such as system 1500 (of FIG. 15) that is configured to collect voltage signal data from the sensors, amplify the signal, convert the signal to a digital signal, and transmit the digital signal to one or more user (mobile) devices. See above.

Once the desired data has been collected from the stacked strain gauge sensors, the stacked strain gauge sensors are removed from the body surface(s). See step 1706. To do so, a liquid adhesive remover (e.g., acetone and/or GBL) is applied to the sensor stack. For instance, the adhesive remover can be dabbed, brushed, sprayed, etc. onto the sensor stack and the body surface surrounding the sensor stack. When attached to the fingernails, the sensor stack can also be soaked in the adhesive remover. The applied remover permeates the glue matrix at several fronts including through the stack due to the through holes. Accordingly, quick release of the adhesive bond is achieved.

Although illustrative embodiments of the present invention have been described herein, it is to be understood that the invention is not limited to those precise embodiments, and that various other changes and modifications may be made by one skilled in the art without departing from the scope of the invention.

What is claimed is:

1. A method, comprising:
   forming multiple sensor layers by depositing strain gauge sensor wires on substrates;
   forming holes in the substrates;
   stacking the formed multiple sensor layers, one on top of another, to form a stack with the formed holes aligned in one or more locations forming through holes in the stack; and
   forming interconnects in the holes in one or more other locations interconnecting the strain gauge sensor wires between adjacent sensor layers to form a stacked strain gauge sensor.

2. The method of claim 1, wherein the strain gauge sensor wires have a serpentine configuration.

3. The method of claim 1, wherein the strain gauge sensor wires comprise a material selected from the group consisting of: an electrically conductive paste, a metal, a metal alloy, a doped semiconductor material, and combinations thereof.

4. The method of claim 1, wherein the depositing further comprises:
   printing the strain gauge sensor wires on the substrates.

5. The method of claim 1, wherein each of the substrates comprises:
   a cover film; and
   a backing film attached to the cover film by an adhesive layer.

6. The method of claim 5, wherein the cover film comprises a release film coated with a release agent.

7. The method of claim 5, wherein the backing film comprises a material selected from the group consisting of: polyurethane, polyester, polyimide, and combinations thereof.

8. The method of claim 5, wherein the adhesive layer comprises an adhesive selected from the group consisting of: an acrylate adhesive, an acrylic adhesive, and combinations thereof.

9. The method of claim 8, wherein the adhesive layer comprises cyanoacrylate glue.

10. The method of claim 1, wherein the stacked strain gauge sensor has a footprint with dimensions of less than or equal to 15 mm×15 mm.

11. The method of claim 1, wherein the stacked strain gauge sensor is configured to fit on a body surface.

12. The method of claim 11, wherein the stacked strain gauge sensor is attachable to the body surface with an adhesive.

13. The method of claim 11, wherein the body surface comprises a fingernail.

* * * * *